(12) United States Patent
Felix et al.

(10) Patent No.: US 10,335,258 B2
(45) Date of Patent: *Jul. 2, 2019

(54) PROSTHESIS FOR REPAIRING A HERNIA DEFECT

(71) Applicant: C.R. Bard, Inc., Murray Hill, NJ (US)

(72) Inventors: Augustus Felix, Cranston, RI (US); Jason Hamilton, Dartmouth, MA (US); John Conidi, Plainville, MA (US); Matthew Rothberg, Marlborough, MA (US); Donald E. Ziniti, Cumberland, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 145 days.

This patent is subject to a terminal disclaimer.

(21) Appl. No.: 15/389,943

(22) Filed: Dec. 23, 2016

(65) Prior Publication Data

US 2017/0181831 A1   Jun. 29, 2017

Related U.S. Application Data

(60) Provisional application No. 62/271,888, filed on Dec. 28, 2015.

(51) Int. Cl.
*A61F 2/00* (2006.01)
(52) U.S. Cl.
CPC .... *A61F 2/0063* (2013.01); *A61F 2002/0068* (2013.01); *A61F 2002/0072* (2013.01);
(Continued)
(58) Field of Classification Search
CPC ........ A61F 2250/001; A61F 2210/0014; A61F 2210/0004; A61F 2210/0076;
(Continued)

(56) References Cited

U.S. PATENT DOCUMENTS

| 460,940 A | 10/1891 | Baugh |
| 5,116,357 A | 5/1992 | Eberbach |
| (Continued) | | |

FOREIGN PATENT DOCUMENTS

| EP | 0 557 964 A1 | 9/1993 |
| EP | 1 971 275 B1 | 11/2009 |
| (Continued) | | |

OTHER PUBLICATIONS

International Search Report and Written Opinion for International Application No. PCT/US2016/068537, dated Jun. 14, 2017, 18 pages.

(Continued)

*Primary Examiner* — David C Eastwood
*Assistant Examiner* — Erich Herbermann
(74) *Attorney, Agent, or Firm* — Wolf, Greenfield & Sacks, P.C.

(57) ABSTRACT

A prosthesis for repairing a hernia defect includes a patch body, a hoisting frame releasably attachable to the patch body, and a tether attached to the hoisting frame with a free end extendable through the thickness of the patch body and accessible from the side of the patch body opposite to where the hoisting frame is releasably attached. The patch body and/or the hoisting frame includes a self-expanding support member. The hoisting frame includes a frame body with an outer frame component and a force translation component for directing pulling forces on the tether across the frame body. The outer frame component has a loop configuration to generally follow the patch periphery with overlapping end portions or a gap between free ends thereof. The force translation component is separable into multiple segments to facilitate withdrawal of the hoisting frame through an opening when released from the patch.

13 Claims, 8 Drawing Sheets

(52) U.S. Cl.
CPC .............. *A61F 2210/0004* (2013.01); *A61F 2210/0014* (2013.01); *A61F 2210/0076* (2013.01); *A61F 2220/0025* (2013.01); *A61F 2220/0075* (2013.01); *A61F 2230/0006* (2013.01); *A61F 2230/0008* (2013.01); *A61F 2230/0039* (2013.01); *A61F 2230/0058* (2013.01); *A61F 2250/001* (2013.01)

(58) Field of Classification Search
CPC ...... A61F 2002/0072; A61F 2002/0068; A61F 2220/0075; A61F 2230/0039; A61F 2230/0008; A61F 2230/0058; A61F 2230/0006; A61F 2/0063
See application file for complete search history.

(56) References Cited

U.S. PATENT DOCUMENTS

| | | | |
|---|---|---|---|
| 5,141,515 A | 8/1992 | Eberbach | |
| 5,147,374 A | 9/1992 | Fernandez | |
| 5,176,692 A | 1/1993 | Wilk et al. | |
| 5,258,000 A | 11/1993 | Gianturco | |
| 5,333,624 A | 8/1994 | Tovey | |
| 5,366,460 A | 11/1994 | Eberbach | |
| 5,368,602 A | 11/1994 | de la Torre | |
| 5,370,650 A | 12/1994 | Tovey et al. | |
| 5,395,383 A | 3/1995 | Adams et al. | |
| 5,397,332 A | 3/1995 | Kammerer et al. | |
| 5,405,360 A | 4/1995 | Tovey | |
| 5,634,931 A | 6/1997 | Kugel | |
| 5,797,960 A | 8/1998 | Stevens et al. | |
| 5,824,082 A | 10/1998 | Brown | |
| 5,916,225 A | 6/1999 | Kugel | |
| 5,919,232 A | 7/1999 | Chaffringeon et al. | |
| 5,957,939 A | 9/1999 | Heaven et al. | |
| 6,258,113 B1 | 7/2001 | Adams et al. | |
| 6,391,060 B1 | 5/2002 | Ory et al. | |
| 6,565,590 B2 | 5/2003 | Kieturakis et al. | |
| 6,575,988 B2 | 6/2003 | Rousseau | |
| 6,616,685 B2 | 9/2003 | Rousseau | |
| 6,702,827 B1 | 3/2004 | Lund et al. | |
| 6,911,037 B2 | 6/2005 | Gainor et al. | |
| 7,235,042 B2 | 6/2007 | Vanden Hoek et al. | |
| 7,273,489 B2 | 9/2007 | Boudjemline | |
| 7,377,936 B2 | 5/2008 | Gainor et al. | |
| 7,824,420 B2 | 11/2010 | Eldridge et al. | |
| 7,947,054 B2 | 5/2011 | Eldar et al. | |
| 8,388,633 B2 | 3/2013 | Rousseau et al. | |
| 8,500,762 B2 | 8/2013 | Sholev et al. | |
| 8,562,633 B2 | 10/2013 | Cully et al. | |
| 9,439,643 B2 | 9/2016 | Darois et al. | |
| 9,504,548 B2 | 11/2016 | Darois et al. | |
| 9,642,689 B2 | 5/2017 | Sholev et al. | |
| 10,034,736 B2 | 7/2018 | Blackburn et al. | |
| 10,172,700 B2 | 1/2019 | Hamilton et al. | |
| 10,182,899 B2 | 1/2019 | Felix et al. | |
| 2002/0103494 A1 | 8/2002 | Pacey | |
| 2002/0133236 A1 | 9/2002 | Rousseau | |
| 2004/0019360 A1 | 1/2004 | Farnsworth et al. | |
| 2004/0087980 A1 | 5/2004 | Ford et al. | |
| 2005/0049635 A1 | 3/2005 | Leiboff | |
| 2005/0171569 A1 | 8/2005 | Girard et al. | |
| 2006/0015143 A1 | 1/2006 | Alvarado | |
| 2006/0247586 A1 | 11/2006 | Voegele et al. | |
| 2007/0066980 A1 | 3/2007 | Leahy | |
| 2007/0185506 A1 | 8/2007 | Jackson | |
| 2007/0260179 A1 | 11/2007 | Sholev et al. | |
| 2007/0265710 A1 | 11/2007 | Brown et al. | |
| 2008/0065229 A1 | 3/2008 | Adams | |
| 2008/0195121 A1 | 8/2008 | Eldar et al. | |
| 2009/0254103 A1 | 10/2009 | Deutsch | |
| 2009/0270999 A1 | 10/2009 | Brown | |
| 2010/0069947 A1 | 3/2010 | Sholev et al. | |
| 2010/0241145 A1 | 9/2010 | Cook | |
| 2010/0261953 A1 | 10/2010 | Townsend et al. | |
| 2010/0261954 A1 | 10/2010 | Townsend et al. | |
| 2010/0261956 A1 | 10/2010 | Townsend et al. | |
| 2010/0292718 A1 | 11/2010 | Sholev et al. | |
| 2011/0011407 A1 | 1/2011 | Townsend et al. | |
| 2011/0054500 A1 | 3/2011 | Levin et al. | |
| 2011/0112560 A1 | 5/2011 | Sholev | |
| 2011/0118706 A1 | 5/2011 | Gingras et al. | |
| 2011/0152897 A1 | 6/2011 | Bates | |
| 2011/0224704 A1 | 9/2011 | Bailly et al. | |
| 2011/0288567 A1 | 11/2011 | Ranucci et al. | |
| 2011/0295283 A1 | 12/2011 | Darois et al. | |
| 2012/0065649 A1 | 3/2012 | Towler | |
| 2013/0035704 A1 | 2/2013 | Dudai | |
| 2013/0060263 A1 | 3/2013 | Bailly et al. | |
| 2013/0103042 A1 | 4/2013 | Davis | |
| 2013/0103058 A1 | 4/2013 | Gobran | |
| 2013/0178876 A1 | 7/2013 | Horton et al. | |
| 2013/0218178 A1 | 8/2013 | Shandas | |
| 2013/0218179 A1 | 8/2013 | Sholev et al. | |
| 2013/0231526 A1 | 9/2013 | Felix et al. | |
| 2013/0267970 A1 | 10/2013 | Cardinale et al. | |
| 2014/0025093 A1 | 1/2014 | Horton et al. | |
| 2014/0051915 A1 | 2/2014 | Sholev et al. | |
| 2014/0058416 A1 | 2/2014 | Brown | |
| 2014/0088343 A1 | 3/2014 | Arcand et al. | |
| 2014/0088619 A1 | 3/2014 | Cardinale et al. | |
| 2014/0188250 A1 | 7/2014 | Fearnot et al. | |
| 2015/0148824 A1 | 5/2015 | Horton et al. | |
| 2015/0157437 A1 | 6/2015 | Cohen et al. | |
| 2015/0209129 A1 | 7/2015 | Bailly et al. | |
| 2015/0250576 A1 | 9/2015 | Blackburn et al. | |
| 2015/0257866 A1* | 9/2015 | Filipiak ................ A61F 2/0063 606/151 |
| 2016/0151136 A1 | 6/2016 | Hamilton et al. | |
| 2017/0100229 A1 | 4/2017 | Darois et al. | |
| 2017/0181832 A1 | 6/2017 | Felix et al. | |
| 2017/0181833 A1 | 6/2017 | Felix et al. | |
| 2018/0311025 A1 | 11/2018 | Blackburn et al. | |

FOREIGN PATENT DOCUMENTS

| | | |
|---|---|---|
| EP | 1 336 391 B1 | 12/2011 |
| FR | 2 769 825 A1 | 4/1999 |
| WO | WO 03/002029 A1 | 1/2003 |
| WO | WO 2007/087146 A2 | 8/2007 |
| WO | WO 2007/115110 A2 | 10/2007 |
| WO | WO 2010/027898 A1 | 3/2010 |
| WO | WO 2010/039249 A1 | 4/2010 |
| WO | WO 2010/059234 A1 | 5/2010 |
| WO | WO 2011/137224 A1 | 11/2011 |
| WO | WO 2012/047414 A1 | 4/2012 |
| WO | WO 2013/007534 A1 | 1/2013 |
| WO | WO 2013/007535 A1 | 1/2013 |
| WO | WO 2013/048272 A1 | 4/2013 |
| WO | WO 2013/049791 A1 | 4/2013 |
| WO | WO 2013/049795 A1 | 4/2013 |
| WO | WO 2013/062933 A1 | 5/2013 |
| WO | WO 2013/142353 A1 | 9/2013 |
| WO | WO 2013/148719 A1 | 10/2013 |
| WO | WO 2013/148839 A1 | 10/2013 |

OTHER PUBLICATIONS

Invitation to Pay Additional Fees for International Application No. PCT/US2016/068537, dated Apr. 18, 2017.

International Preliminary Report on Patentability for International Application No. PCT/US2016/068537, dated Jul. 12, 2018.

* cited by examiner

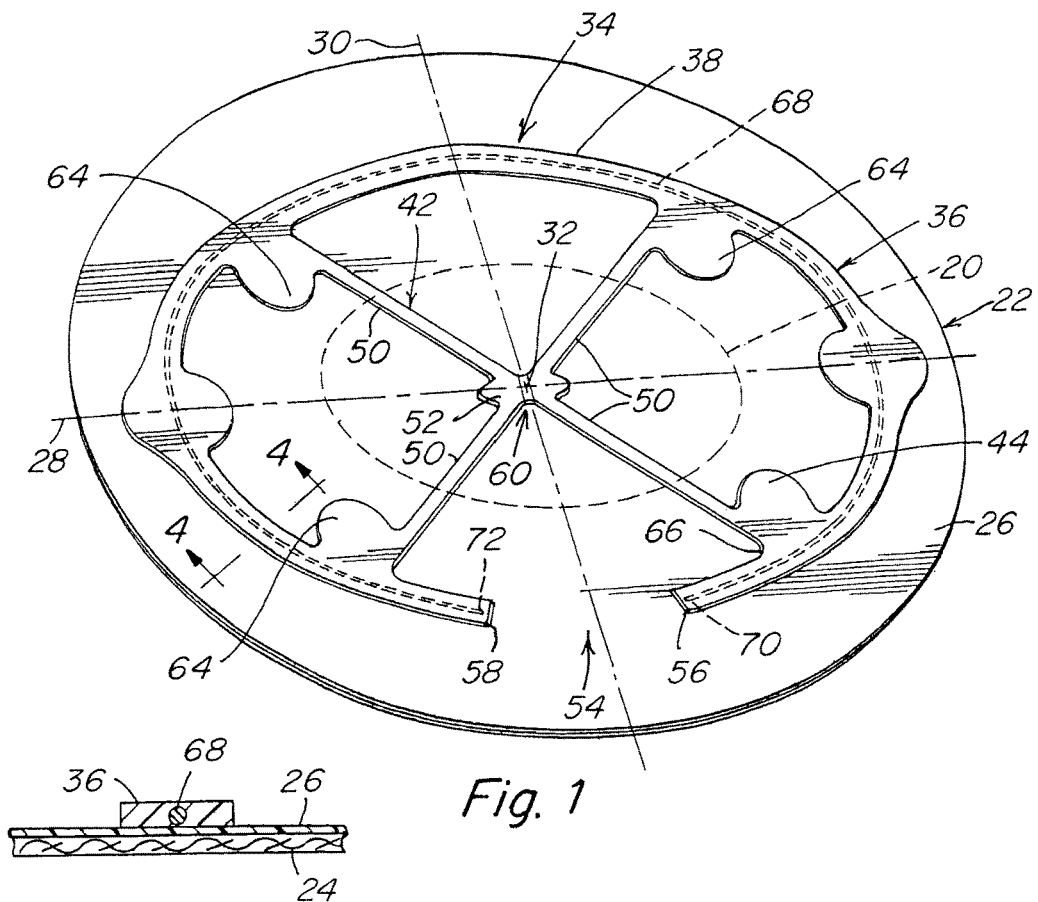
Fig. 1
Fig. 4
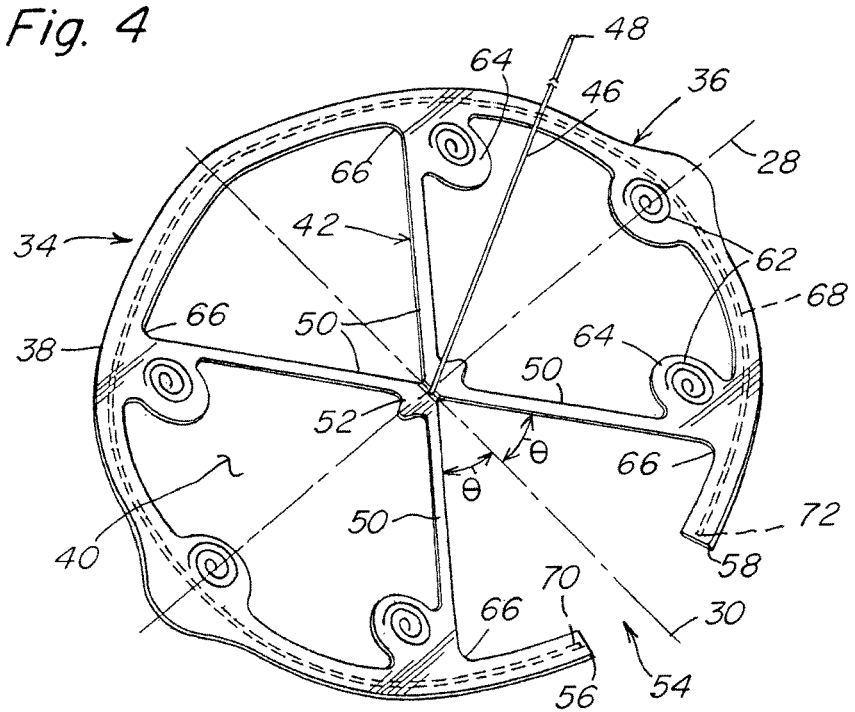
Fig. 2

PROSTHESIS FOR REPAIRING A HERNIA DEFECT

FIELD

A prosthesis for repairing a hernia defect.

BACKGROUND

A hernia defect is an opening or weakness in a tissue or muscle wall, such as the abdominal wall. One approach for repairing a hernia is to cover the tissue or muscle wall defect with a patch of repair fabric. The patch may be placed in an open procedure or through a minimally invasive procedure, such as by a laparoscopic technique.

In a laparoscopic hernia repair, a patch is delivered through a narrow cannula to a treatment site within the patient. Because the patch is much larger than the cannula bore, the patch must be reduced in size to enable passage through the small opening into the patient. After laparoscopic deployment, the patch needs to return to an enlarged shape sufficient to cover the defect. Some hernia repair patches include a resilient support member, such as an elastic wire, that is collapsed along with the patch into a reduced configuration and delivered through the laparoscopic cannula. After exiting the cannula, the resilient support member unfurls causing the associated patch to expand into the enlarged repair configuration. The expanded patch including the resilient support member is then fixated to the tissue or muscle wall over the defect.

SUMMARY

According to one aspect, a prosthesis for repairing a hernia defect comprises a patch body having a periphery, and a self-expanding hoisting frame releasably attachable to the patch body to assist in spreading the patch body from a reduced configuration to an expanded configuration. The hoisting frame includes an outer frame component and a force translation component, the outer frame component defining an open interior and the force translation component extending through the open interior. A tether is attached to the force translation component. A free end of the tether is extendable away from the force translation component and through the patch body when the hoisting frame is releasably attached to the patch body. A pulling force on the free end of the tether in an outward direction away from the patch body is directed by the force translation component in the direction of the outer frame component when the patch body is in the expanded configuration. The patch body and the hoisting frame when releasably attached to the patch body are manipulable into the reduced configuration for insertion through an opening into a patient. The force translation component is configured to be separated into a plurality of segments to facilitate withdrawal of the hoisting frame through the opening when the hoisting frame is released from the patch body.

According to another aspect, a prosthesis for repairing a hernia defect comprises a patch body having a periphery, and a self-expanding hoisting frame releasably attachable to the patch body to assist in spreading the patch body from a reduced configuration to an expanded configuration. The hoisting frame includes an outer frame component and a force translation component, the outer frame component defining an open interior and the force translation component extending through the open interior. The outer frame component includes a first free end and a second free end. The outer frame component extends continuously about the open interior from the first free end to the second free end thereof. A tether is attached to the force translation component. A free end of the tether is extendable away from the force translation component and through the patch body when the hoisting frame is releasably attached to the patch body. A pulling force on the free end of the tether in an outward direction away from the patch body is directed by the force translation component in the direction of the outer frame component when the patch body is in the expanded configuration. The patch body and the hoisting frame when releasably attached to the patch body are manipulable into the reduced configuration for insertion through an opening into a patient.

According to another aspect, a prosthesis for repairing a hernia defect comprises a patch body having a periphery, and a self-expanding hoisting frame releasably attachable to the patch body to assist in spreading the patch body from a reduced configuration to an expanded configuration. The self-expanding hoisting frame includes an outer frame component and a force translation component, the outer frame component defining an open interior and the force translation component extending through the open interior. A tether is attached to the force translation component. A free end of the tether is extendable away from the force translation component and through the patch body when the hoisting frame is releasably attached to the patch body. A pulling force on the free end of the tether in an outward direction away from the patch body is directed by the force translation component in the direction of the outer frame component when the patch body is in the expanded configuration. A self-expanding support member is coupled to the outer frame component to assist in expanding the hoisting frame from a reduced configuration to an expanded configuration. The support member is coupled to the outer frame component to constrain movement of the support member at one or more first regions of the outer frame component while allowing movement of the support member at one or more second regions of the outer frame component in response to manipulating the hoisting frame from the expanded configuration to the reduced configuration. The movement of the support member is greater at the one or more second regions than at the one or more first regions. The patch body and the hoisting frame when releasably attached to the patch body are manipulable into the reduced configuration for insertion through an opening into a patient.

According to another aspect, a method is provided for repairing a hernia defect. The method comprises an act of (a) delivering a prosthesis in a reduced configuration through an opening into a patient. The prosthesis includes a patch body and a self-expanding hoisting frame releasably attached to the patch body to assist in spreading the patch body to an expanded configuration. The self-expanding hoisting frame includes an outer frame component and a force translation component. The outer frame component defines an open interior and the force translation component extends through the open interior to direct force applied thereto in the direction of the outer frame component when the patch body is in the expanded configuration. The method further comprises acts of: (b) following act (a), spreading the patch body to the expanded configuration via the hoisting frame, (c) securing the patch body in the expanded configuration about the hernia defect, (d) separating the force translation component into a plurality of segments to facilitate withdrawal of the hoisting frame, (e) following act (c), detaching the hoisting frame from the patch body, and (f) withdrawing the hoisting frame through the opening out of the patient.

According to another aspect, a method is provided for repairing a hernia defect. The method comprises an act of: (a) delivering a prosthesis in a reduced configuration through an opening into a patient. The prosthesis includes a patch body and a self-expanding hoisting frame releasably attached to the patch body to assist in spreading the patch body to an expanded configuration. The self-expanding hoisting frame includes an outer frame component and a force translation component, the outer frame component defining an open interior and the force translation component extending through the open interior to direct force applied thereto in the direction of the outer frame component when the patch body is in the expanded configuration. The outer frame component includes a first free end and a second free end spaced, the outer frame component extending continuously about the open interior from the first free end to the second free end thereof. The method further comprises acts of: (b) following act (a), spreading the patch body to the expanded configuration via the hoisting frame, (c) securing the patch body in the expanded configuration about the hernia defect, (d) following act (c), detaching the hoisting frame from the patch body, and (e) withdrawing the hoisting frame out of the patient by pulling one of the first and second free ends of the outer frame component through the opening so that the hoisting frame is extended lengthwise with the other of the first and second free ends trailing the hoisting frame through the opening.

According to another aspect, a method is provided for repairing a hernia defect. The method comprises an act of: (a) manipulating a prosthesis from an expanded configuration to a reduced configuration for delivery through an opening into a patient. The prosthesis includes a patch body and a self-expanding hoisting frame releasably attached to the patch body to assist in spreading the patch body to an expanded configuration. The self-expanding hoisting frame includes an outer frame component, a self-expanding support member and a force translation component, the outer frame component defining an open interior and the force translation component extending through the open interior to direct force applied thereto in the direction of the outer frame component when the patch body is in the expanded configuration. The support member is coupled to the outer frame component to assist in expanding the hoisting frame from the reduced configuration to the expanded configuration. The method further comprises an act of: (b) constraining movement of the support member at one or more first regions of the outer frame component while outward movement of the support member occurs at one or more second regions of the outer frame component in response to manipulation of the prosthesis. The method further comprises acts of: (c) following act (a), delivering the prosthesis through the opening into the patient in the reduced configuration, (d) following act (c), spreading the patch body to the expanded configuration via the hoisting frame causing inward movement of the support member at the one or more second regions of the outer frame component, (e) securing the patch body in the expanded configuration about the hernia defect, (f) following act (e), detaching the hoisting frame from the patch body, and (g) withdrawing the hoisting frame through the opening out of the patient.

BRIEF DESCRIPTION OF DRAWINGS

Aspects of the invention are described below, by way of example, with reference to the accompanying drawings in which like numerals reference like elements, and wherein:

FIG. 1 is an illustration of a prosthesis for repairing a hernia defect with an assembled hernia repair patch and hoisting frame in an expanded configuration;

FIG. 2 is an illustration of a patch body side of a hoisting frame with a tether extending from the hoisting frame;

FIG. 4 is sectional illustration along line 4-4 of FIG. 1;

DETAILED DESCRIPTION

Figure 3:
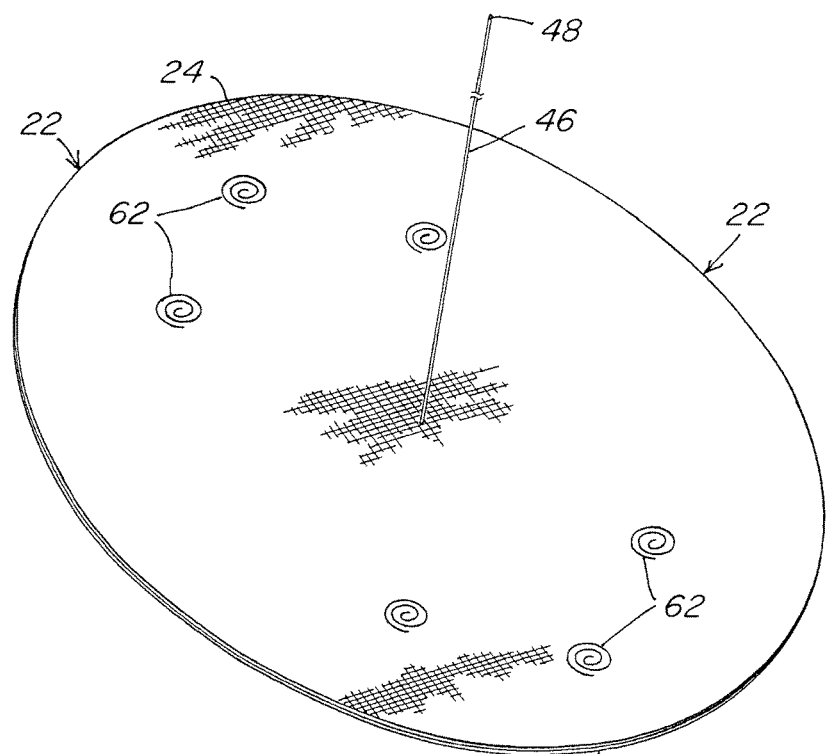
FIG. 3 is an illustration of an assembled patch body, frame and tether, with fixation components securing the patch body to the frame and the tether extending from the frame through the thickness of the patch body and being accessible on the side of the patch body opposite the frame body.

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

Various embodiments are described in connection with the repair of a hernia, specifically a ventral hernia. However, the invention is not necessarily so limited, and may be employed to repair other types of hernias, other soft tissue or muscle wall defects, as well as may be used in other surgical or medical treatments. With respect to repair of a ventral hernia, the repair patch may be placed in the intraperitoneal, preperitoneal, retromuscular, or other anatomical space, as the invention is not so limited. For ease of understanding, the hernia repair patch is described in connection with a laparoscopic procedure but may be employed in other minimally invasive procedures, in an open procedure, or in other techniques for repairing a hernia or other soft tissue defect as should be apparent to one of skill in the art.

A patch for repairing a hernia may include a patch body having a first side that will be positioned against a tissue or muscle wall, such as the abdominal wall, that includes the defect. The first side of the patch body may be configured for tissue ingrowth. Where the patch will be located adjacent sensitive organs, such as the intestines or other viscera, an opposite side of the patch body may include a barrier, such as a layer of barrier material or a barrier coating, to prevent adhesions between the first side of the patch and the sensitive organs.

In a minimally invasive technique, as well as in certain open procedures, a hernia repair patch may be reduced in size to facilitate delivery of the prosthetic device to the treatment site. For example, in a laparoscopic procedure, a hernia repair patch may be rolled into a slender cylindrical shape, or otherwise collapsed into a smaller configuration, suitable for passage through a narrow cannula which may have an inner diameter of approximately 15 mm to approximately 5 mm, or of even a finer size. After delivery to the surgical site, the reduced hernia repair patch is transformed into an expanded configuration. The enlarged patch is then placed against the abdominal wall and may be fixated by sutures, staples, tacks and/or other fixation elements. For example, such fixation elements may be applied through a border region, and/or at other locations, of the patch into healthy tissue surrounding the defect.

A hoisting frame may be employed to provisionally hold the expanded patch against the abdominal wall pending fixation. The hoisting frame may include a frame body and fixating components at various locations on the frame body to releasably attach the hoisting frame to the patch. Such locations may be in the form of lands, other portions of the frame body, and other regions of the frame body as should be apparent to one of skill in the art. The hoisting frame may be compliant to facilitate its collapsibility when the assembled patch and hoisting frame are rolled up or otherwise reduced in shape for minimally invasive delivery.

A tether may extend from the hoisting frame and be passed through the patch body so that its free end is accessible on the side of the patch body opposite to the hoisting frame. When the assembled patch and hoisting frame have unfurled or otherwise opened to an expanded shape at the surgical site, the tether may be drawn through the abdominal wall to outside of the patient. Continued pulling of the tether will draw the frame, and the patch body supported by the frame, upwardly against the abdominal wall.

The frame body may include an outer frame component and a force translation component configured so that a pulling force on the tether in an outward direction away from the hoisting frame and the patch body is directed by the force translation component in different directions toward the outer frame component. Such a translation of the pulling force in different direction towards regions or portions of the outer frame component assists in spreading the hoisting force about the frame body.

The outer frame component may be configured to generally follow the periphery of the patch body and define a generally open interior through which fixation elements, such as sutures, tacks, staples or other suitable fasteners, may be applied to secure the patch body to adjacent tissue and/or muscle. For example, and without limitation, the outer frame component may have a generally annular shape with a loop-like configuration. Representative shapes of an outer frame component include, but are not limited to, circular, oval or a polygon.

To facilitate release and withdrawal of the hoisting frame, the outer frame component may be provided with free ends at opposite ends of the outer frame component. In this manner, the outer frame component may have a loop configuration extending continuously from one free end to the other free end and about most or all of the open interior and the patch periphery. An outer frame component with free ends permits the hoisting frame, including the outer frame component, to be drawn, stretched or otherwise extended into a generally elongated configuration either during or following release of the frame from the patch body.

According to one aspect, the free ends of the outer frame component may be spaced apart from each other to define a gap therebetween. The gap may have any width suitable for providing a hoisting frame configuration with sufficient structure to provisionally hold the expanded patch against the abdominal wall while also facilitating its release and withdrawal.

According to another aspect, the outer frame component may include a pair of end segments terminating at the free ends which may be configured to overlap each other at an overlap region therebetween. The end segments may be releasably coupled together at the overlap region. For example, and without limitation, one of the end segments may include a retainer, such as a pocket, to releasably receive and retain the other end segment to couple the end segments to each other.

A loop configuration with free ends may also assist in reducing potential tissue entrapment as the hoisting frame is withdrawn from a patient following securement of the patch body. For example, a loop configuration which can be drawn or stretched into a generally elongated configuration may reduce the ability of the hoisting frame to potentially pinch or scoop tissue and/or intestine as the frame is collapsed and withdrawn from a patient. Pinching of tissue could potentially occur due to the collapsing action of a closed loop frame, which does not include free ends, as it is drawn into a cannula during withdrawal from a patient. Scooping could potentially occur when a closed loop frame snares intestine as the frame is drawn into a cannula during withdrawal.

The force translation component extends across and/or through the open interior of the frame body and connects to the outer frame component at a plurality of locations to transmit the pulling force on the tether across the frame body. The force translation component may be configured to be separated into two or more segments to facilitate reconfiguration of the hoisting frame into the generally elongated configuration for withdrawal from a patient.

The force translation component may include one or more separation regions preformed at locations where separation is desirable. Each separation region may also be configured to separate in one or more predetermined directions. A separation region may employ any suitable arrangement that allows the force translation component to separate by applying a sufficient amount of force to the region. For example, and without limitation, the separation region may employ relatively weak or thin material as compared to adjacent material, perforations forming a tear line, and/or one or more score lines that permit separation along the region.

Rather than separating the force translation component by force, the separation region may employ an arrangement in which the force translation component includes separate segments coupled together using one or more fastening elements, such as suture, fasteners, or adhesive as should be apparent to one of skill, which can be removed or otherwise permit separation of the segments of the force translation component. The fastening element holds the segments together in a manner to allow transmission of the pulling force through the frame body. If desired, a tether or tether segments may extend from each of the segments of the force translation component to ensure the pulling force is applied directly to each of the separable or separated segments.

The force translation component may include a plurality of force translation arms which direct forces to various regions of the outer frame component. The arms may extend from a central portion of the force translation component in an outward radial direction to the outer frame component. The arms may be arranged to transmit force to opposing sides of the outer frame component. For example, and without limitation, the arms may be arranged in an X-shape with the central portion located at an approximate center of the frame. Other patterns of translation arms are contemplated; for example, the arms may have an H-shape or other configuration as should be apparent to one of skill in the art. The force translation component may be configured so as to be non-self-expanding. That is, the force translation component may be compliant but not notably resilient nor possessing shape memory.

The arms may be integrally formed with the central portion as a unitary structure that may be separated into separate arms by applying a sufficient amount of force to the central portion. Alternatively, the arms may be separate segments with individual free ends that are coupled together at the central region. For example, and without limitation, the free ends of the arms may be arranged in a stacked configuration and coupled together with the hoisting frame tether.

To assist in unfurling the patch into an expanded shape after minimally invasive deployment, a support member may be associated with the hoisting frame and/or the patch body. The support member may have a resiliency or other property (e.g., shape memory) that allows the support member to deform from an initial, expanded, shape into a compact configuration as the patch is reduced in size for laparoscopic or other minimally invasive delivery, and then return to the initial shape, or at least to a shape larger than the reduced shape, upon reaching the delivery site. Such an ability to revert from a reduced configuration to an expanded configuration without requiring assistance of a medical professional is referred to herein as a "self-expanding" support member. Recovery of the support member causes the patch to spread out into an expanded configuration. For example, and without limitation, the support member may be rollable into a reduced size for delivery to the hernia repair site.

A representative support member may be formed from a nitinol wire. It is also contemplated that the support member may be formed of a multi-strand, braided wire. The support member may be configured to assume a relatively straight configuration in its resting state so that the support member becomes loaded when deformed into a desired shape for coupling to the frame body. In this manner, the support member becomes preloaded when reconfigured and coupled to the frame body in a loop arrangement so that the support member urges the hoisting frame to an elongated configuration when separated from the patch body. For some applications, the support member may be coated or covered with a dielectric material, such as ethylene tetrafluoroethylene (ETFE) or perfluoroalkoxy (PFA), to protect the support member from potential contact with an electrocautery device during a surgical procedure.

The support member may have a frame-like shape and/or may generally follow the periphery of the patch. Representative shapes of a support member include circular, oval or a polygon. The support member may have a generally planar configuration in the extended condition. Alternatively, one or more portions of the support member, such as the free ends of an open loop configuration, may be formed out of plane to tent the patch at a desired location.

The support member may include a single length of wire that follows the periphery of the patch or frame. Alternatively, the support member may include multiple lengths of wire spaced apart from each other in the radial direction relative to the central portion with one length of wire spaced inwardly from another length of wire. The multiple lengths of wire may be formed from a single wire that is shaped to form a pair of looped end portions spaced apart to define the free ends of an open loop configuration.

The support member may be contained within the frame body, attached to the surface of the frame body, woven in undulating fashion through the frame body, or otherwise associated with the frame body. When associated with the frame body, the hoisting frame is referred to as being "self-expanding". The support member may be configured to extend along the outer frame component, and may employ an open or overlapping loop arrangement that corresponds with an outer frame component having an open or overlapping loop configuration. If desired, the support member may also extend along portions of the force translation component. In addition, or alternatively, it also is contemplated to form the frame body with self-expanding properties.

The support member may be coupled to the frame body to fully or partially constrain movement, such as outward radial movement, of the support member relative to the frame body as the hoisting frame is manipulated between expanded and reduced configurations. In a fully constrained arrangement, movement of the support member is minimized during manipulation of the hoisting frame. For example, and without limitation, the support member may be mounted within a channel provided along the outer frame component and constrained by the sides of the channel extending along and in close proximity to the support member. In a partially constrained arrangement, movement of the support member may be constrained at one or more regions of the frame body while allowing movement of the support member in a desired direction at one or more other regions of the frame body in response to manipulating the hoisting frame from the expanded configuration to the reduced configuration. For example, and without limitation, a pocket configured to accommodate movement of the support member may be provided at each region where it is desired to allow movement. Each pocket may be provided at a selected region of the channel of the outer frame component in which is mounted the support member. For example, and without limitation, a pair of pockets may be provided at opposite ends of the outer frame along the axis about which the hoisting frame may be rolled into a reduced configuration. Such an arrangement allows the pockets to accommodate growth of the support member length along the roll axis to minimize the load on the fixating components which releasably attach the hoisting frame to the patch body.

The hoisting frame may have a thin profile to provide a reduced configuration when collapsed with the patch body for minimally invasive delivery. The frame body may be in the form of a flat sleeve (e.g., sheath), for example from opposed thin pieces of fabric such as NYLON that are fused or otherwise joined together, at least in those portions of the frame where a self-expanding support member will be contained therein. The force translation component extending between opposite edges of the outer frame component may be formed of the same material that constitutes the outer frame component or of a different material. In either case, the force translation component also may present a thin profile to provide a slender shape when the frame and patch body are rolled up or otherwise collapsed for minimally invasive delivery.

The tether may be in the form of a suture, a strap such as a strip of mesh fabric, a combination suture and strap, or constructed from other or additional components as should be apparent to one of skill in the art. The tether may be tied to, bonded or fused with, or otherwise attached by any appropriate method with, the force translation component. Alternatively, the force translation component and the tether may be integrally formed together as a unitary structure. In certain embodiments, the force translation component extends to various fixating components for releasably connecting the hoisting frame to the patch body.

The hoisting frame, and the support member when located remote from the hoisting frame, may be characterized by their positioning relative to the axes of the patch body. For example, the frame and the support member where disassociated from the frame, may include a first portion that is positionable on an upper portion of the patch body relative to a first axis, and a second portion that is positionable on an opposite, lower portion of the patch body relative to the first axis. Each of the first portion and the second portion may have a curved profile, although straight, compound straight, angled and/or curved, and other profiles are contemplated as should be apparent to one of skill in the art. The hoisting frame, and the support member when not associated with the hoisting frame, may include lateral and medial portions which may have similar or different profiles as compared to the top and bottom portions.

With the patch body spread out over the hernia defect, and secured to the tissue or muscle wall, the inventors have recognized that there no longer is need for the hoisting frame and associated support member. Accordingly, the hoisting frame, as observed earlier, may be releasably attached to the hernia repair patch, allowing selective removal of the hoisting frame and associated support member by the surgical team after expanding, positioning, and/or fixation of the patch body. Detachment of the frame will, in turn, separate the support member if associated with the frame, from the fixated patch body. The detached frame and associated support member may then be removed from the patient, such as by withdrawal through the same narrow opening in which the patch and hoisting frame had been delivered minimally invasively into the patient. Withdrawal may be facilitated by separating the force translation component at one or more separation regions and pulling a free end of the outer frame component to draw or stretch the frame into a generally elongated configuration that may more readily pass through the narrow opening used for delivering the patch and hoisting frame.

In one embodiment, the releasable fixating components for connecting the frame to the patch body include a coil-type fixating component that are provided at various locations, such as at a land or projection, about the frame body. The coil-type fixating component may have an extended, linear configuration that facilitates passing the fixating component into, and removing the fixating component from, the patch body and a retracted, coiled configuration which retains the patch body. Other arrangements for releasably attaching the frame to the patch body also are contemplated. For example, and without limitation, a suture may run between the frame, such as at a land, and the patch body. The suture can be cut at one or more locations and then the frame pulled away from the patch body. Alternatively, the suture may be sufficiently weak or be modified to include one or more localized weak points that will fail upon application of a sufficient pulling force. Alternatively, the frame, such as at a land, may be adhered by a relatively weak adhesive to the patch body. Another option is to configure the frame and/or patch body so as to releasably engage each other. In one such arrangement, the patch body may include one or more slits that releasably receive an aspect of the frame.

The frame body and patch body may have generally the same shape or different shapes. For example, the patch body could be rectangular and the frame body oval. In one embodiment, the hoisting frame includes a generally oval frame body that contains a generally oval self-expanding support member. Both the frame body and the support member may have gaps aligned with each other so as to form an open loop configuration. A force translation component, such as X-shaped arms, extends between top and bottom aspects of the oval portion of the hoisting frame. At or near the junction of the translation arms and the oval portion of the frame body are fixating components for releasably attaching the hoisting frame to a patch body. The fixating components, such as coil fasteners, may be located on lands that extend interiorly and/or exteriorly of the oval portion of the frame.

As shown in FIGS. 1-6, a prosthesis for repairing a hernia or other soft tissue defect 20 may include a patch body 22 having a first surface 24 that is arranged for tissue ingrowth and a second surface 26 that is configured as a barrier to adhesions between the first surface and sensitive organs or tissue, such as the intestines or other viscera. The first surface may include a tissue infiltratable layer such as a mesh or other porous fabric amenable to tissue ingrowth, and the second surface may be a solid or substantially non-porous barrier layer or a barrier coating that will prevent contact between the viscera and the porous tissue ingrowth fabric. The patch body 22 may be defined by a first axis 28 and a second axis 30 that is substantially perpendicular to the first axis. The intersection of the first and second axes may coincide with a center, or approximate center 32, of the patch body. Alternative arrangements of a patch body are contemplated as should be apparent to one of skill in the art. For example, and without limitation, the patch body may include only a tissue infiltratable layer, only a solid or non-tissue infiltratable layer, or a combination of tissue infiltratable and non-tissue infiltratable aspects situated in the same layer.

A hoisting frame 34 may be positioned adjacent the second surface 26 and may extend generally around the periphery of the patch body, as illustrated in FIG. 1. The frame may have a thin or reduced profile and, for example and without limitation, may be in the form of a flat sleeve or sheet so as to minimize the overall thickness of the patch when assembled with the frame and reduced for delivery through an opening, such as a narrow incision or cannula, to the treatment site. The frame may be a continuous component or may include two or more discrete segments that are contiguous and/or spaced from each other which in combination form a frame body.

In one illustrative embodiment, a frame body 36 may include an outer frame component 38 which defines a generally open interior space 40 through which fixation elements such as sutures, tacks, staples or other devices may be applied to secure the patch body to the abdominal wall. The frame body may also include a force translation component 42 extending across the open frame body interior and connected to the outer frame component. In addition, or alternatively, the force translation component may be connected to portions 44 of the frame body supporting the fixating components that releasably attach the hoisting frame to the patch body and/or to other portions of the frame body. A portion of the force translation component extends through a central region of the frame.

A tether 46 may extend from the central region of the frame body. A free end 48 of the tether is passed through the thickness of the patch body 22 so that it extends beyond the side of the patch body opposite the hoisting frame. During the procedure, the tether may be drawn through the abdominal wall to outside of the patient. A pulling force on the free end of the tether in an outward direction away from the hoisting frame and the patch body is directed by the force translation component 42 to the junction of the force translation component and the fixating component support portions 44 and/or the outer frame component 38. The resultant translated forces spread the pulling force about the frame body, facilitating hoisting of the frame and associated patch body against the abdominal wall.

The force translation component 42 may include a plurality of force translation arms 50 which direct forces to various regions of the outer frame component. The arms may extend from a central portion 52 of the force translation component in an outward radial direction to the outer frame component 38. The arms may be arranged to transmit force to opposing sides of the outer frame component. As illustrated, the arms 50 may be arranged in an X-shape with the central portion 52 located at an approximate center of the frame. Other patterns of the force translation component are contemplated; for example, the force translation component may be arranged to have an H-shape or other configuration suitable to transmit the pulling force on the tether to outward and lateral aspects of the frame body and/or fixation components as should be apparent to one of skill in the art.

In one illustrative embodiment, the force translation arms 50 may be arranged in first and second pairs of arms on opposite sides of the first axis 28. The pairs of arms may be further arranged with the arms 50 of each pair located on opposite sides of the second axis 30. In this manner, the force translation component 42 may be arranged with an arm 50 located in each quadrant defined by the first and second axes with each arm extending from the central portion 52 at or near the approximate center of the frame body. Although the force translation component is shown with arms that are symmetric about the first and second axes, they need not be so as should be apparent to one of skill in the art. That is, the force translation component may be asymmetric about one or both of the first and second axes of the hoisting frame.

The force translating component 42 may be configured with each arm 50 having an angle θ relative to the second axis for directing the translated forces to the outer frame component. In one embodiment, the angle θ may range from 70 degrees to 5 degrees on each side of the second axis. For example, and without limitation, the direction of the translated forces may be +/−30°, +/−45°, or such other combination of force direction relative to the second axis (where "+" is one side of the axis and "−" is the other side of the axis). The direction of forces by the force translation component on one side of the axis need not mirror the direction of forces on the other side of the axis, nor need the forces translated towards one portion of the outer frame component have the same direction as the forces transmitted towards another portion of the outer frame component. For example, and without limitation, the force translation component could be configured to direct forces at +/−30° relative to the axis at a first portion and +/−45° relative to the axis at a second portion on opposite sides of the axis.

To facilitate release and withdrawal of the hoisting frame following securement of the patch body at the hernia defect, the frame body may be configured to permit the hoisting frame, including the outer frame component, to be drawn or stretched into a generally elongated configuration either during or following release of the frame from the patch body. Such an arrangement may be desirable when withdrawing the hoisting frame through a narrow opening, such as a minimally invasive cannula.

In one illustrative embodiment, the outer frame component 38 may have an open loop configuration with a gap 54 defined by opposite free ends 56, 58 spaced apart from each other across the gap. In this manner, the outer frame component extends continuously from one free end 56 to the other free end 58 and about a substantial portion of the patch periphery. The width of the gap may be selected to provide the hoisting frame with sufficient structure to hold the expanded patch against the abdominal wall while also facilitating its release and withdrawal.

As shown, the gap 54 may be located entirely on one side of the first axis 28 and along the second axis 30. In one embodiment, the first and second free ends 56, 58 of the outer frame component 38 are located on opposite sides of the second axis 30 with the gap being centered on the second axis. As shown, the gap may be located between a pair of the force translation arms 50. As should be apparent to one of skill in the art, the gap may be located along any portion of the outer force component suitable for reconfiguring the hoisting frame into a generally elongated configuration.

To enhance the ability of the hoisting frame to be reconfigured for withdrawal through a narrow opening, the force translation component 42 may be arranged to be separated into two or more segments. In this regard, the force translation component may include one or more separation regions preformed at locations where separation is desirable. Each separation region may also be configured to separate in one or more predetermined directions.

Figure 6:
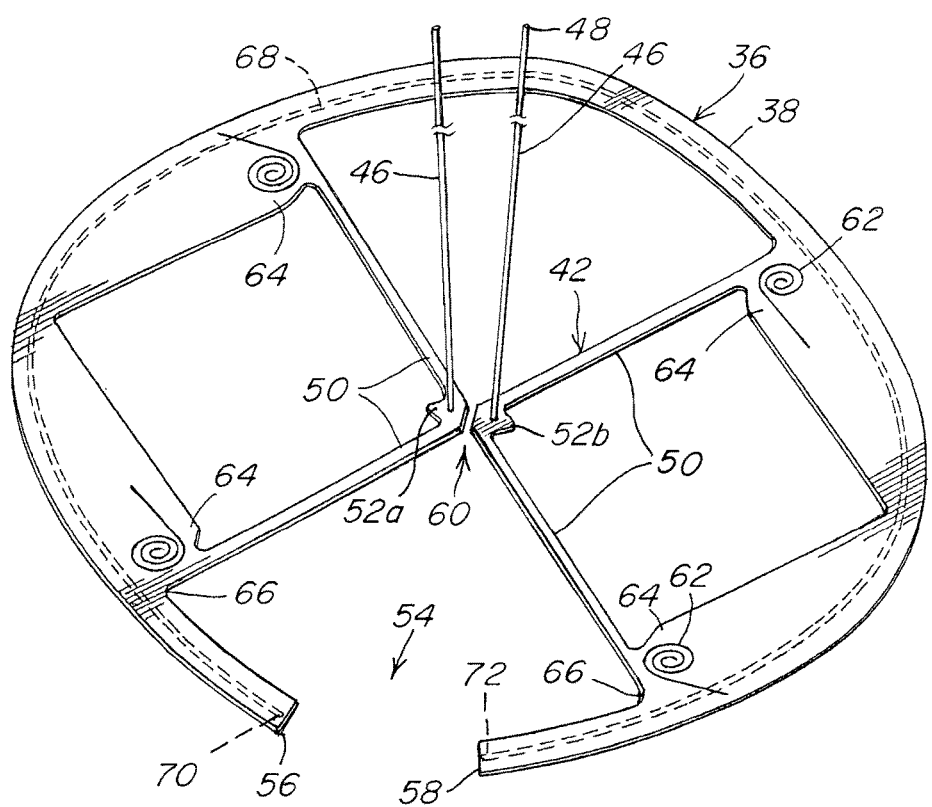
FIG. 6 is an illustration of a patch body side of the hoisting frame of FIG. 5 with a central portion of the force translation component separated into segments to facilitate withdrawal of the hoisting frame.

In one illustrative embodiment, the central portion 52 of the force translation component may be configured to be separated into a plurality of segments where separation of the central portion causes at least two of the force translation arms 50 to separate from each other to facilitate collapse of the hoisting frame. The central portion 52 may include a separation region 60 configured to be separated in a direction along the second axis 30. As shown in FIG. 6, such an arrangement results in separation of the arms 50 on one side of the second axis 30 from the arms 50 on the opposite side of the second axis.

Figure 5:
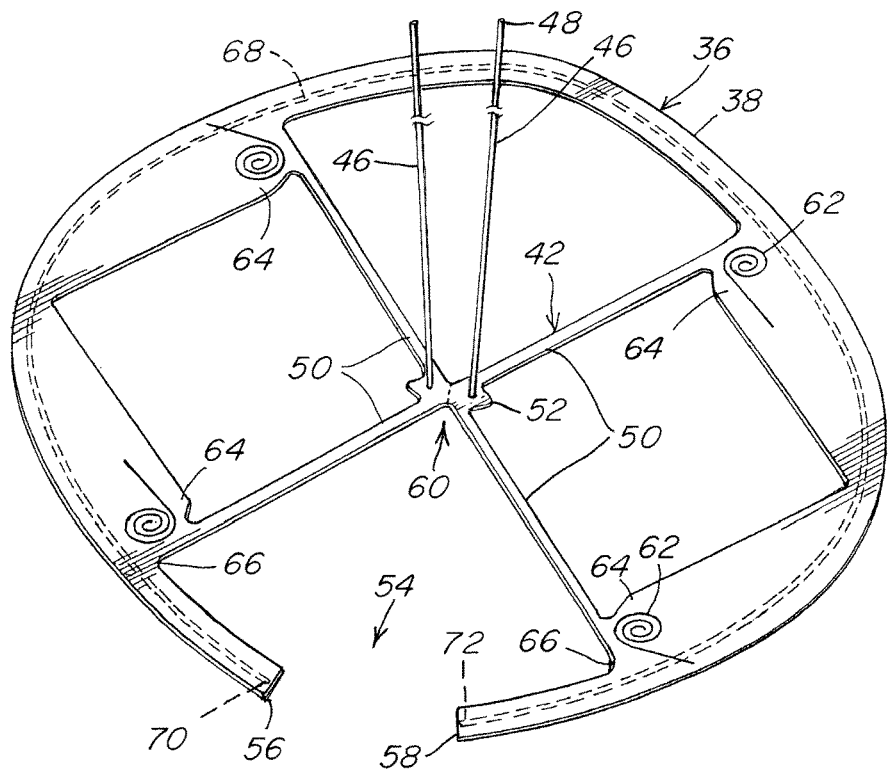
FIG. 5 is an illustration of a patch body side of an alternative hoisting frame with a pair of tethers extending from the hoisting frame.

The separation region 60 may employ any suitable arrangement that allows the force translation component 42 to separate into segments by applying a sufficient amount of force to the region. For example, and without limitation, the separation region may employ relatively weak or thin material as compared to adjacent material, employ perforations that form a tear line, and/or employ one or more score lines which permit separation along the region. Alternatively, the separation region 60 may employ an arrangement in which the force translation component 42 includes separate segments, such as separated central portion segments 52a, 52b as shown in FIG. 6, coupled together using one or more fastening elements, such as suture, fasteners, or adhesive as should be apparent to one of skill, which can be removed or otherwise allow separation of the segments of the force translation component. The fastening element may hold the segments together in a manner to allow transmission of the pulling force through the frame body. If desired, as shown in FIGS. 5-6, a tether 46 or tether segments may extend from each of the segments of the force translation component to ensure the pulling force is applied directly to each of the separable or separated segments 52a, 52b.

The frame may be releasably attached to the patch body via one or more fixating components 62. In one embodiment, the fixating component has an unretracted configuration, such as substantially straight, that is adapted to attach or detach the fixation component to the patch body, thus allowing connection or release of the patch body from the hoisting frame. The fixating component has a retracted configuration, such as substantially coiled, to retain the patch body to the fixation component and, in turn, the hoisting frame. One end of the fixating component may be connected to the frame body, such as at a land 64. If desired, the land or other portion of the frame body connected to the fixating component may be reinforced to reduce potential pull out of the fixating component from the frame body. A free end of the fixating component may be sharpened or otherwise adapted to pierce through the patch body. Thus, in the unretracted configuration, the free end of the fixating component may be passed through the patch body and will remain passed through the patch body to retain the patch to the frame when in the retracted configuration.

The fixating components 62 may be located anywhere along the frame body including at land portions 64 of the frame. The fixating components may be positioned at or near portions of the force translation component 42 including, but not limited to, at or near portions of the junction 66 of the force translation component and the frame body. Fixation components may additionally, or alternatively, be located along either axis of the frame body. As illustrated, fixation components 62 may be positioned at lands along the first axis 28 at opposite sides of the frame body. In certain embodiments, the outer frame component, the lands, and the force translating component, lie in the same plane and present a thin, planar profile when the frame body is in an expanded configuration.

The peripheral portion of the frame body 36 may be enlarged at various locations to enhance support of the hernia repair patch when the patch and frame body have been unfurled. FIGS. 5-6, for example, show bulked segments of a frame body at opposite ends of the frame and about a first axis as compared to the frame body illustrated in FIG. 2. The enlarged segments may include the land portions 64 at which the fixation components 62 are positioned.

Contained within the frame body may be a self-expanding support member 68, such as an elastic wire, that will assist in unfurling the patch body into an expanded shape after laparoscopic delivery to the treatment site. The support member 68 may be formed of nitinol, other super-elastic metals, appropriately resilient metals, plastics or other materials, other shape memory metals or plastics, and comparable materials as should be apparent to one of skill in the art. The self-expanding support member may be continuous or formed of two or more spaced segments. The self-expanding support member may have any appropriate shape for transforming the patch body into a desired expanded shape. Representative shapes include, but are not limited to, circular, oval or a polygon, as well as combinations of different shapes to provide a desired amount of support for expanding the frame and patch and manipulation for reducing the frame and patch for delivery through an opening, such as a narrow incision or cannula.

In one embodiment, the support member 68 may be configured to assume a relatively straight shape in its unstressed resting state. When the support member is bent or otherwise reconfigured into a desired shape, such as a loop, without taking a set, the support member becomes preloaded so that it can automatically return to its straight resting state configuration. In this manner, when the support member is preloaded and coupled to the frame body, the support member will urge the hoisting frame to an elongated configuration when separated from the patch body.

For some applications, the support member may be coated or otherwise covered with a dielectric material to protect the support member from potential contact with an electrocautery device during a surgical procedure. In one embodiment, the support member may be covered with ethylene tetrafluoroethylene (ETFE) or perfluoroalkoxy (PFA). However, it is to be appreciated that other suitable dielectric materials may be used to coat or cover the support member, if desired, as should be apparent to one of skill in the art.

As illustrated in FIGS. 1-6, the support member 68 may have a frame-like shape configured to generally follow the periphery of the patch. The support member may extend along the outer frame component 38 to form a self-expanding outer frame component. The support member may have a continuous configuration and include a pair of free ends 70, 72 that terminate in the vicinity of the free ends 56, 58 of the outer frame component 38. In this manner, the support member 68 has an open-loop configuration, similar to the outer frame component, with a gap in alignment with the gap in the outer frame component.

The support member 68 may have a generally planar configuration in the extended condition. Alternatively, one or more portions of the support member, such as the end portions of the open loop configuration, may be formed out of plane to tent the patch at a desired location.

As illustrated in FIGS. 1-6, the support member 68 may include a single support component, such as a length of wire, that follows the periphery of the patch or frame outer component. Alternatively, as illustrated in FIGS. 7-10, the support member may include multiple support components, such as lengths of wire, spaced apart from each other in the radial direction relative to the central portion with one support component spaced inwardly from another support component. In one embodiment, the multiple support components may be formed from a single wire that is shaped to form a pair of looped end portions spaced apart to define the free ends of the open loop configuration. Alternatively, the support member may include multiple lengths of wire spaced apart from each other for support and manipulation.

Figure 7:
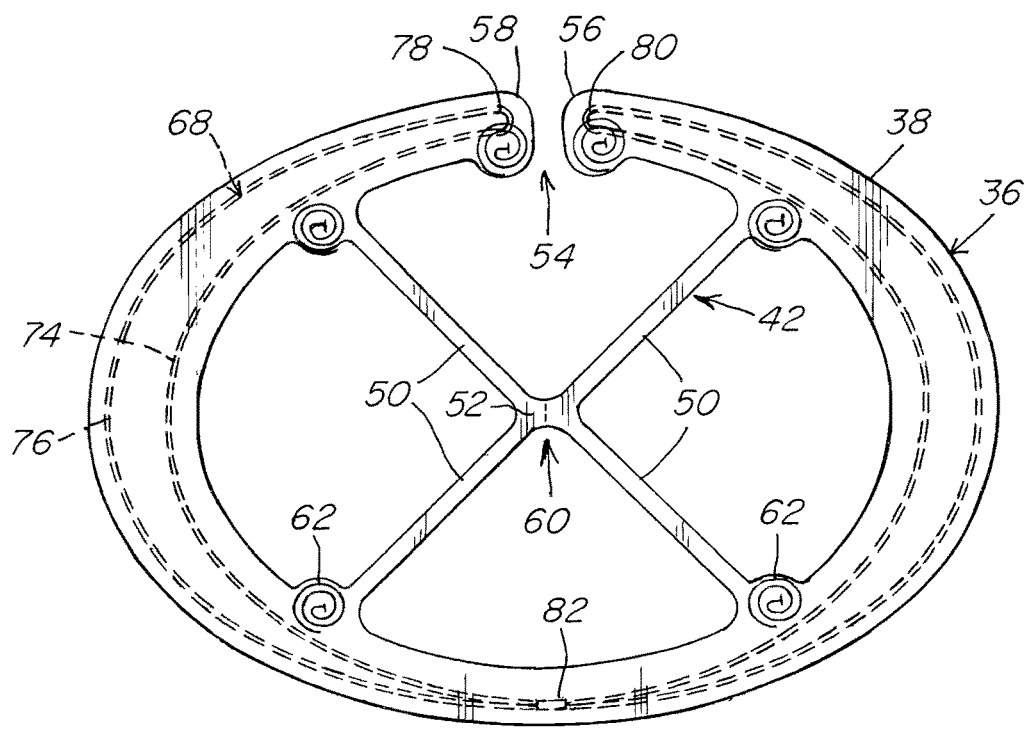
FIGS. 7-10 are illustrations of alternative embodiments of a support member for the hoisting frames of FIGS. 1-6.
Figure 8:
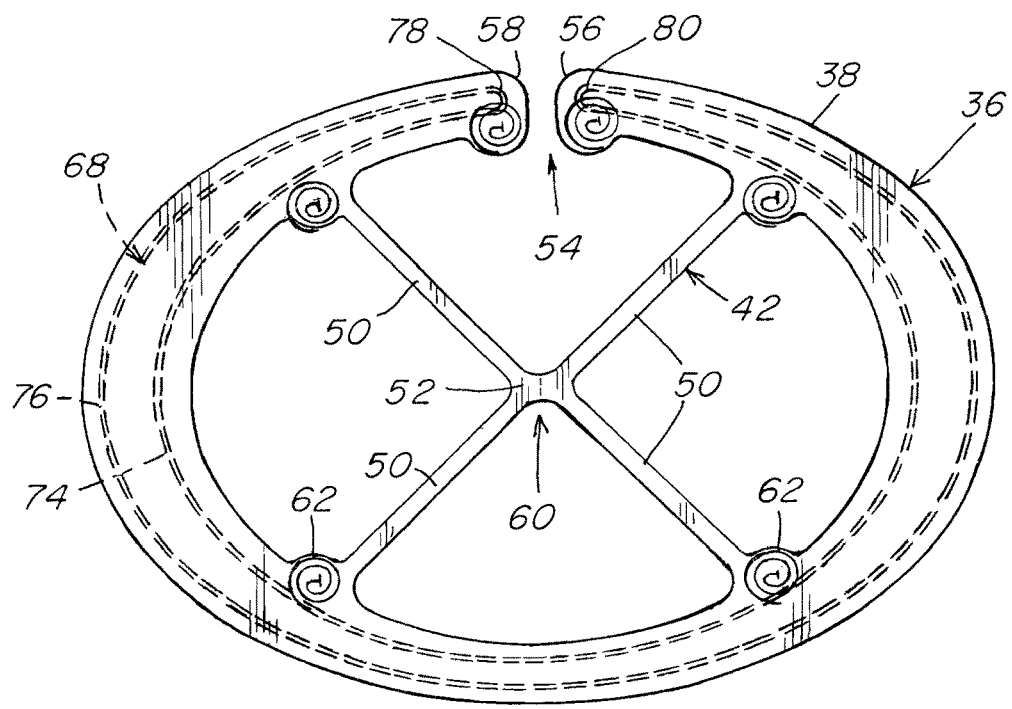

In illustrative embodiments shown in FIGS. 7-8, the support member 68 includes a pair of support components 74, 76 with curved configurations extending along the outer frame component 38 with the free ends of the support components coupled together in looped ends 78, 80 spaced apart to form the gap in an open loop configuration. As shown in FIG. 7, the support components may be coupled together at a region 82 opposite the gap 54 to reduce the rotation of the support member. In one embodiment, the support components may be crimped together, although any suitable technique may be employed as should be apparent to one of skill. As shown in FIG. 8, the spacing between the support components 76, 78 may be maintained along their entire lengths to create more support structure.

Figure 9:
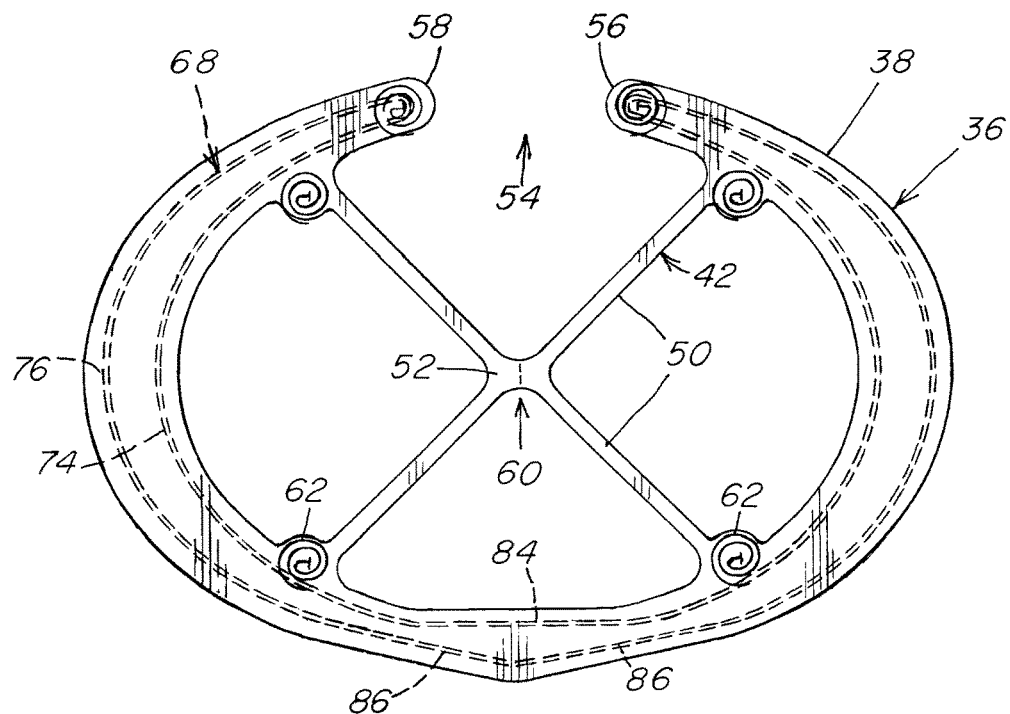

In an illustrative embodiment shown in FIG. 9, curvature in the support components may be eliminated along a portion of the support member opposite the gap to increase the rigidity of the support member. As shown, the inner support component 74 may include a single straight segment 84 and the outer support component 76 may include a pair of straight segments 86. However, it is contemplated that other combinations of curved and straight segments for the support member may be implemented as should be apparent to one of skill to vary the rigidity of the support member.

Figure 10:
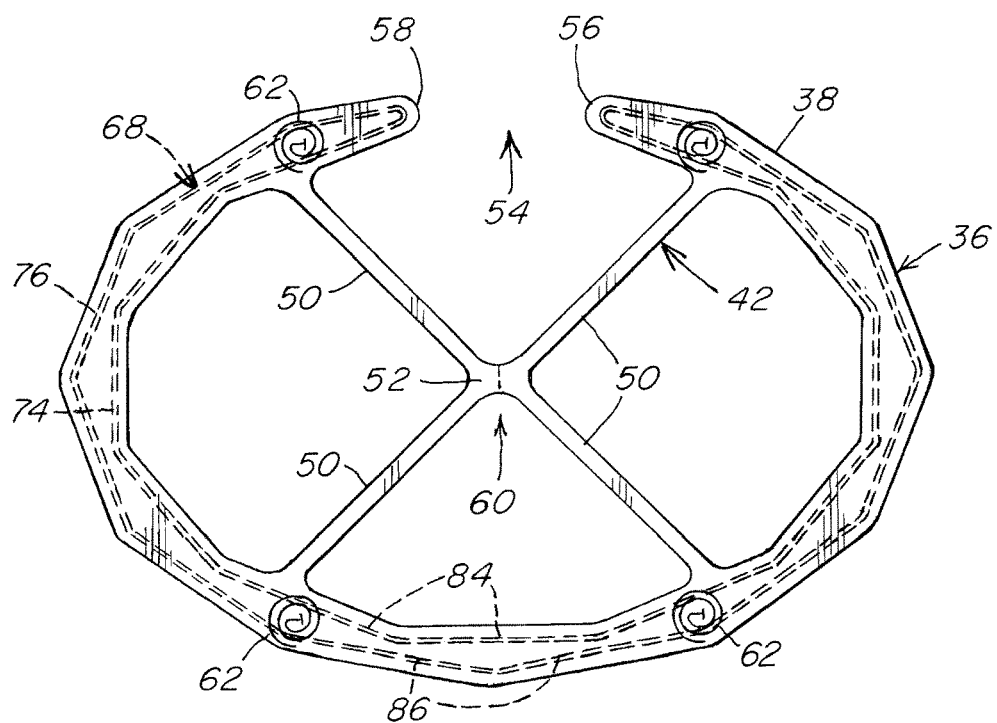

In an illustrative embodiment shown in FIG. 10, curvature in the support components may be eliminated entirely from the support member 68 for additional rigidity as compared to the support member of FIG. 9. As shown, the inner and outer support components 74, 76 may include a series of straight segments 84, 86 that extend along the length of the outer frame component in a generally polygonal shape. However, it is contemplated that other non-curved configurations for the support member may be implemented as should be apparent to one of skill. As shown in FIG. 10, the fixating components 62 may be located between the inner and outer support components.

As indicated above, the frame body may be configured to permit the hoisting frame, including the outer frame component, to be drawn or stretched into a generally elongated configuration either during or following release of the frame from the patch body. In one embodiment as described above, the outer frame component may have an open loop configuration with a gap defined by opposite free ends spaced apart from each other across the gap. However, for some applications, it may be desirable to use an outer frame member which extends completely about the open interior to provide additional support to the patch body, but which can still be drawn or stretched into a generally elongated configuration.

Figure 11:
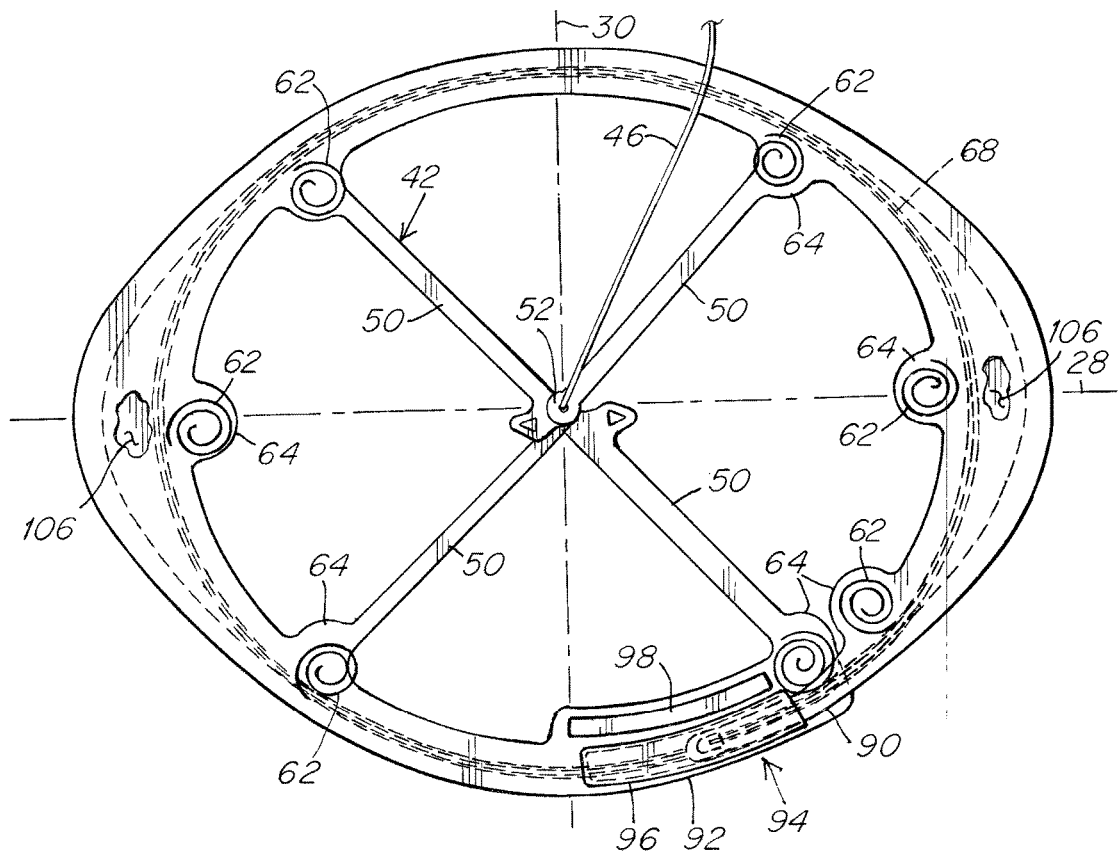
FIG. 11 is an illustration of a patch body side of an alternative hoisting frame including an outer frame component with overlapping end segments.
Figure 12:
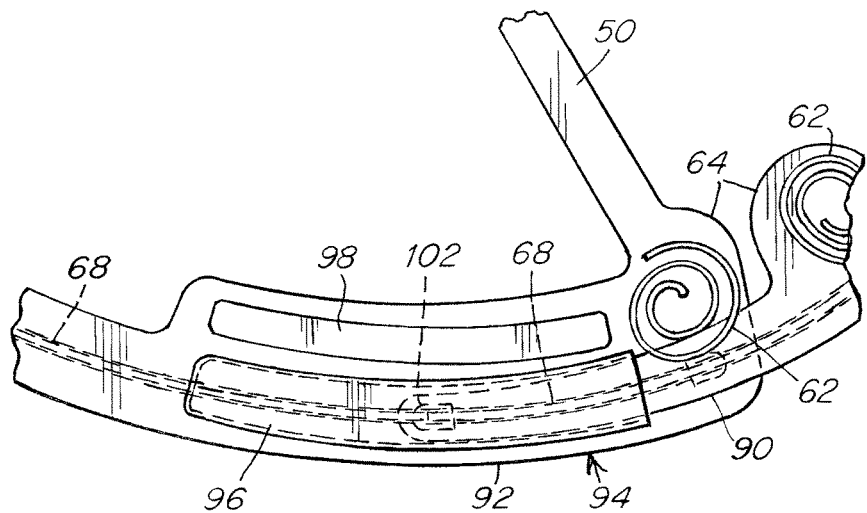
FIG. 12 is an enlarged view of the overlap region of the outer frame component of FIG. 11.
Figure 13:
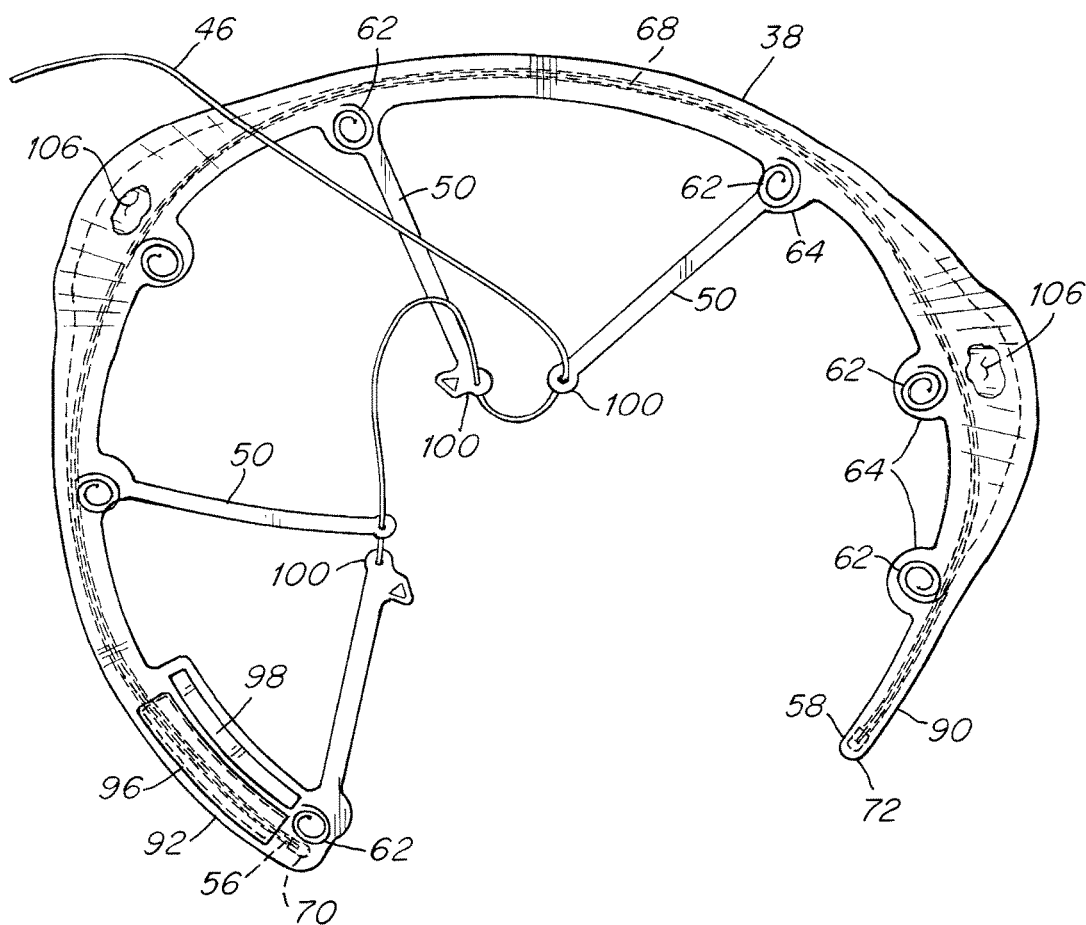
FIG. 13 is an illustration of the hoisting frame of FIG. 11 with the end segments of the outer frame component and the arms of the force translation component being separated to facilitate withdrawal of the hoisting frame.

In an illustrative embodiment shown in FIGS. 11-13, the frame body 36 includes an outer frame component 38 with free ends 56, 58 at opposite ends thereof. The outer frame component is configured to extend continuously and completely about the open interior space 40 from a first free end 56 to a second free end 58 thereof. As shown, the outer frame component includes a first end segment 90 terminating at the first free end and a second end segment 92 terminating at the second free end overlapping each other to define an overlap region 94 therebetween. In this manner, the outer frame component employs a separable loop configuration that provides continuous support about the entire peripheral region of the patch body, but can be drawn or stretched into a generally elongated configuration to facilitate withdrawal of the hoisting frame.

To help retain the outer frame component in a loop configuration, particularly when the outer frame component is preloaded in the loop configuration, the end segments 90, 92 may be releasably coupled together at the overlap region 94. In this manner, the end segments are restrained against separation due to a preload which otherwise urges the outer frame component and the hoisting frame to an elongated configuration. In one embodiment, a retainer, such as a pocket 96, may be provided on one of the end segments to releasably receive the other of the end segments and couple the end segments to each other. For example, the end segments 90, 92 may be slidably coupled together with the pocket. As should be appreciated, other suitable coupling arrangements between the end segments may be employed as should be apparent to one of skill in the art. Retention of the outer frame component may be further enhanced by locating a fixating component 62 adjacent each end segment for connection with the patch body.

In one illustrative embodiment, the overlap region 94 may be located between the first axis 28 and the second axis 30 of the hoisting frame. However, the overlap region may be provided at other suitable locations as should be apparent to one of skill in the art. For example, and without limitation, the overlap region may be located along either the first axis 28 or the second axis 30. If desired, the overlap region may be centered on the first axis or the second axis.

During a surgical procedure, the hoisting frame may be separated from a patch body secured to tissue and withdrawn from the surgical site using a conventional gripping tool, such as a surgical grasper, as known in the art. The hoisting frame may be provided with one or more designated regions along the outer frame component, or elsewhere, for being grasped by the removal tool. However, the hoisting frame could potentially be grasped essentially anywhere along the outer frame component. As such, the overlap region 94 may be configured so that a grasper is unable to grasp the overlap region to such an extent that it may otherwise prevent separation of the end segments 90, 92 from each other and cause removal of the hoisting frame as a closed loop.

In one illustrative embodiment, the overlap region 94 may include a spacer 98 that is arranged to be engaged and grasped by a surgical grasper while preventing the tool from fully gripping the overlap region. In this regard, the spacer 98 may act as a physical stop to prevent full closure of the jaws of the grasper in the area of the pocket and end segment overlap of the outer frame component. This may be achieved using a spacer having sufficient rigidity to withstand the gripping force applied by the grasper. The spacer may also have a height that is greater than the combined heights of the overlapped end segments 90, 92 and a length that generally corresponds to the length of the overlap region 94. As shown, the spacer 98 may be located inwardly of and extend along the region of overlapped end segments 90, 92. As should be apparent to one of skill in the art, other suitable stop arrangements may be implemented, if desired, to prevent full closure of a grasper on the overlap region of the outer frame component.

As indicated above, the force translation component 42 may be configured to be separated into two or more segments to enhance the ability of the hoisting frame to be reconfigured for withdrawal through a narrow opening. In one illustrative embodiment shown in FIGS. 11 and 13, the force translation component 42 may include a plurality of individual arms 50 extending from the outer frame component 38 to the central portion 52. Each arm 50 includes a free end 100 located opposite the outer frame component which are coupled together at the central portion. In one embodiment, the free ends 100 may be coupled together in a stacked arrangement. As shown in FIG. 13, the tether 46 for hoisting the frame may extend through each of the free ends to couple the arms together. Separation of the free ends of the arms allows the outer frame component to be drawn into a generally elongated configuration to facilitate withdrawal of the hoisting frame from a surgical site.

As described above, a self-expanding support member 68, such as an elastic wire, may be contained within the outer frame component to assist in unfurling the hoisting frame and the patch body into an expanded shape after laparoscopic delivery to the treatment site. The support member 68 may be formed of nitinol, other super-elastic metals, appropriately resilient metals, plastics or other materials, other shape memory metals or plastics, and comparable materials as should be apparent to one of skill in the art. The support member may be coated or otherwise covered with a dielectric material to protect the support member from potential contact with an electrocautery device during a surgical procedure.

Figure 14:
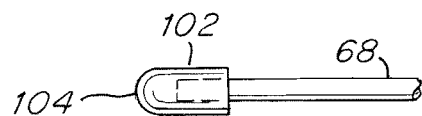
FIG. 14 is an enlarged schematic view of an end segment of the support member with an end cap.

If desired, the outer frame component 38 and/or the free ends 70, 72 of the support member 68 may be configured or otherwise arranged to reduce or prevent puncture through the material of the outer frame component. In one embodiment shown in FIG. 14, the free ends 100 of the support member may be covered with an end cap 102 that is configured to reduce potential penetration of the end segments 90, 92 of the outer frame component. The end caps 102 may also be configured with a rounded nose 104 to present an atraumatic end to tissue should the material of the outer frame component fail and expose the ends of the support member. The ends caps may be formed of a dielectric material, such as polyurethane, ethylene tetrafluoroethylene (ETFE) or perfluoroalkoxy (PFA), to reduce potential coupling of an electrocautery device during surgery. As should be appreciated, the end caps, if employed, may be formed of other suitable material as should be apparent to one of skill in the art.

Because the support member is configured with free ends, it may be desirable to attach or otherwise anchor the ends of the support member 68 to the outer frame component to enhance its functionality associated with rolling and/or deployment of the hoisting frame and the patch body. In one embodiment, the end caps 102 may be secured to the end segments 90, 92 of the outer frame component. For example, the end caps may be impulse welded to the material of the outer fame component. However, other suitable connection techniques may be employed to secure the end caps in place as should be apparent to one of skill in the art.

For some applications, it may be desirable to fully constrain the support member 68 within the outer frame component 38 to minimize movement of the support member relative to the outer frame component. However, for other applications, fully constraining the support member may potentially create excessive force on the connections between the fixating components 62 and the patch body during manipulation, such as associated with rolling and/or deployment, of the hoisting frame and patch body. Thus, for some applications, it may be desirable to partially constrain the support member within the outer frame component. In a partially constrained arrangement, movement of the support member may be constrained at one or more regions of the outer frame component while allowing movement of the support member at one or more other regions of the outer frame component in response to manipulation of the hoisting frame.

Figure 15:
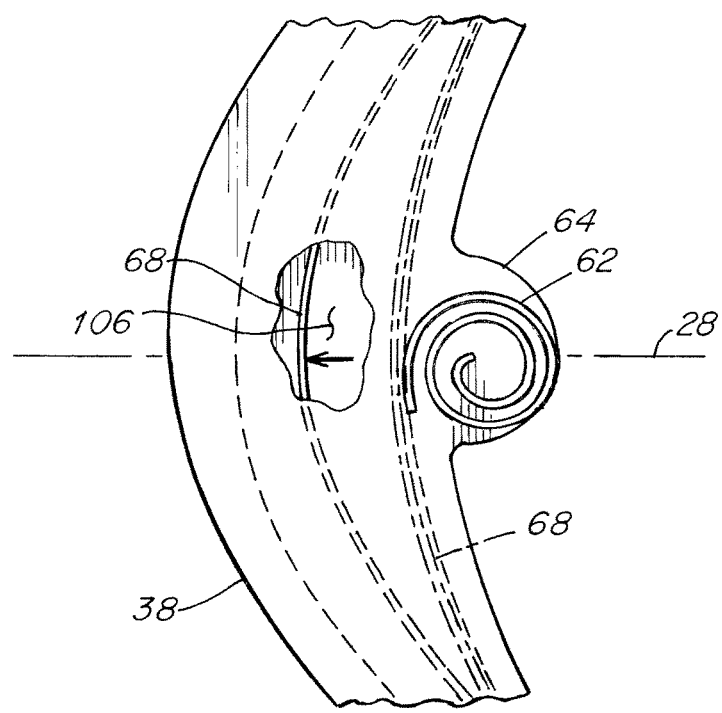
FIG. 15 is an enlarged view of an end pocket provided on the outer frame component of FIG. 11 for accommodating radial movement of the support member.

In one illustrative embodiment, the outer frame component 38 may include one or more pockets 106 to accommodate movement of the support member 68 at one or more desired locations of the outer frame component. Each pocket may be configured to accommodate movement of the support member that occurs during manipulation of the hoisting frame. In one embodiment, a pocket 106 may be provided at each end of the outer frame component 38 along the first axis 28. As shown in FIGS. 11 and 15, such an arrangement allows the support member 68 to essentially grow (as shown by arrow in FIG. 15) in a direction along the first axis 28 as the hoisting frame and patch body are rolled about the first axis. The pockets 106 may be configured to accommodate the maximum growth of the support member during rolling and minimize the load that would otherwise be exerted at the connections between the hoisting frame and the patch body due to a constrained support member. It is to be appreciated that other arrangements suitable for accommodating movement and/or growth of the support member may be employed as should be apparent to one of skill in the art.

In some embodiments, the frame body may be in the form of a thin, flat textile structure having a bottom surface and a top surface, and at least one of the top and bottom surfaces may have a substantially flat shape. In one embodiment, the bottom surface that faces the patch body may have a flat shape, with the top surface having a curved profile. In other embodiments, a wall may be located between the long edges of the top and bottom surfaces. The top and bottom surfaces may be separated only where the support member is sandwiched therebetween. The frame body, then, is solid. The outer frame component may be formed of a NYLON material, other synthetic polymers, as well as natural materials. The force translation component also may be formed of a thin, flat textile structure and may be composed of the same or of different material as the outer frame component. The force translation component may be in the form of a strip, sheath, or spoke, for example, or other suitable force translating configuration as should be apparent to one of skill in the art. In certain embodiments, the force translation component and the outer frame component may be integrally formed as a unitary structure.

Various techniques may be employed to reduce the assembled patch and hoisting frame to a smaller configuration suitable for delivery through a narrow opening, such as via a laparoscopic cannula. For example, and without limitation, the assembled patch and hoisting frame, may be rolled up into a cylinder. In one embodiment, an introducer includes a shaft having a patch receiving area that may be defined, for example, between splined sections of the shaft. The patch receiving area may threadably receive the patch. Rotating the shaft will cause the patch to roll up about the shaft in the area of the patch receiving area.

The patch body 22 may have any form appropriate for repairing a hernia defect. The patch may be substantially flat or may be arranged with a concave, convex, or a combination concave/convex surface. The distance between edges of the patch body along the first axis 28 may be greater than the distance between edges of the patch body along the second axis 30; that is, the patch body may be elongated along the first axis. The shape of the patch body when viewed along the first axis may be different than the shape of the patch body when viewed along the second axis. For example, and without limitation, the edges of the patch body intersected by the first axis may be generally round while the edges of the patch body intersected by the second axis may be linear and run parallel to the first axis. Without wishing to be bound by any theory, the linear edges provide a greater area for threading to the introducer as compared to a patch body having round edges—such as if the patch were circular or oval shaped. Other patch body configurations are contemplated as should be apparent to one of skill in the art.

The patch body 22 may be formed of a porous material, such as a knit fabric, woven or non-woven fabric, or may be composed of a solid, substantially non-porous, or microporous material. The patch body may be formed of one or more layers of the same or dissimilar material, and the layers may be stacked one on top of the other, side-to-side, or include a combination of both stacking arrangements. The patch body may be formed with portions that are tissue infiltratable and other portions that are less tissue infiltratable or are non-tissue infiltratable, providing selected areas of the repair device with different tissue ingrowth and adhesion resistant properties. The patch body may be formed of permanent material, resorbable material, or a combination of permanent and resorbable materials. It should be appreciated that the patch body may be formed of any biologically compatible material, synthetic or natural, suitable for repairing a tissue or muscle wall defect as would be apparent to one of skill in the art.

A representative embodiment of the hernia repair patch and a representative procedure for using same is now described. A hernia repair patch configured to repair a ventral hernia includes a patch body having a tissue infiltratable layer on one side and a barrier layer on the other side. The tissue infiltratable layer may include one or more sheets of surgical mesh fabric, such as a polypropylene knit. The barrier layer may be a sheet of synthetic or natural barrier material; for example, and without limitation, a sheet of ePTFE may be stitched, heat fused or otherwise connected to a polypropylene sheet. Another option is to embed the polypropylene knit into a film of SEPRA (bioresorbable hydrogel barrier). The polypropylene side would face the abdominal wall and the ePTFE or SEPRA side would face the viscera. A flat, generally oval-shaped, annular outer frame component defines a generally open interior that is intersected by flat X-shaped force translating arms. At each intersection of the arms and the outer frame component are enlarged lands that each support a fixating component having an unretracted linear configuration and a retracted coiled configuration. The outer frame component, the force translating arms, and the lands are formed of thin NYLON sheet. A tether in the form of a suture extends from the central portion of the force translation component from which extends the arms forming the X-shape; that is, at the approximate center of the frame body. Contained within the generally oval outer frame component is a 0.020 inch diameter nitinol wire that also is generally oval shaped. The wire is covered with a dielectric to electrically insulate it from potential contact with an electrocautery device during a surgical procedure.

The center of the frame body is registered with the center of the patch body, with the outer frame component generally following the periphery of the patch body. The fixating components are elongated or straightened and passed from the barrier side of the patch body to the tissue infiltratable side, and then allowed to resiliently retract to a coil shape against the tissue infiltratable side, securing the patch body to the hoisting frame. The suture tether is passed through the barrier side and out beyond the tissue infiltratable side where it will be accessible for manipulation to hoist the frame body and associated patch body against the abdominal wall.

The flexible patch and hoisting frame are rolled into a small configuration and then delivered through an opening, such as a narrow incision or cannula, into a patient. Upon exiting the incision or cannula, the nitinol wire springs back to a larger shape, spreading the patch body into an expanded configuration. The suture tether extending from the patch may be pulled through the abdominal wall, such as by a suture passer, and then manipulated outside of the patient to hoist the frame and assembled patch body against the abdominal wall about the defect. A pulling force on the tether in an outward direction away from the frame and the patch body is directed by the translation component towards the upper and the lower portions of the frame body, helping spread the hoisting force about the frame. With the patch positioned against the abdominal wall, fixation elements, such as a suture, tack, or staple, are applied through the periphery of the patch extending outwardly beyond the frame and, or alternatively, through the openings within the interior of the frame body.

With the patch securely fixated to the abdominal wall, the hoisting frame and self-expanding support member may then be detached from the anchored patch. For example, the surgical team may use a grasper or other laparoscopic instrument to grip and pull the frame away from the patch. In response to the pulling force, the resilient fixating components transform to the unretracted configuration (i.e., linear or substantially linear) allowing the fixating components to slide back through the fixated patch body. Prior to or following detachment of the hoisting frame, the central portion of the force translation component may be separated into segments to facilitate withdrawal of the hoisting frame. Once separated from the patch, the frame and associated self-expanding support member may be withdrawn through the same minimally invasive opening, such as a laparoscopic cannula or narrow incision, via which the assembled hoisting frame and patch were originally delivered to the surgical site. This may be accomplished by grasping and pulling a free end of the outer frame component through the minimally invasive opening so that the hoisting frame generally elongates and is extended lengthwise as it is withdrawn through the minimally invasive opening (cannula or narrow incision) with the other free end trailing the frame through the opening to reduce potential pinching and/or scooping of tissue and/or intestine.

For purposes of this patent application and any patent issuing thereon, the indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

The foregoing description of various embodiments are intended merely to be illustrative thereof and that other embodiments, modifications, and equivalents are within the scope of the invention recited in the claims appended hereto.

What is claimed is:

1. A prosthesis for repairing a hernia defect, the prosthesis comprising:
   a patch body having a periphery, a first axis and a second axis perpendicular to the first axis, the first axis and the second axis intersecting at approximately a center of the patch body, a first portion of the patch body on a first side of the first axis and a second portion of the patch body on a second side of the first axis;
   a self-expanding hoisting frame releasably attachable to the patch body to assist in spreading the patch body from a reduced configuration to an expanded configuration, the self-expanding hoisting frame including an outer frame component and an inner frame component configured to translate force, the outer frame component defining an open interior and the inner frame component extending through the open interior; and
   a tether attached to the inner frame component, a free end of the tether extendable away from the inner frame component and through the patch body when the self-expanding hoisting frame is releasably attached to the patch body, a pulling force on the free end of the tether in an outward direction away from the patch body being directed by the inner frame component in a direction toward the outer frame component when the patch body is in the expanded configuration;
   wherein the patch body and the self-expanding hoisting frame when releasably attached to the patch body are manipulable into the reduced configuration for insertion through an opening into a patient; and wherein the inner frame component is configured to be separated into a plurality of segments to facilitate withdrawal of the self-expanding hoisting frame through the opening when the self-expanding hoisting frame is released from the patch body.

2. The prosthesis according to claim 1, wherein the outer frame component is self-expanding.

3. The prosthesis according to claim 2, wherein the inner frame component is non-self-expanding.

4. The prosthesis according to claim 2, wherein the outer frame component includes a self-expanding support.

5. The prosthesis according to claim 1, wherein the outer frame component has a configuration that generally follows the periphery of the patch body.

6. The prosthesis according to claim 5, wherein the outer frame component is spaced inwardly of the periphery of the patch body.

7. The prosthesis according to claim 1, wherein the self-expanding hoisting frame has a first axis and a second axis perpendicular to the first axis, the first and second axes of the self-expanding hoisting frame intersecting at approximately a center thereof, the inner frame component including a central portion located at the center of the self-expanding hoisting frame, the central portion configured to be separated into the plurality of segments to facilitate withdrawal of the self-expanding hoisting frame.

8. The prosthesis according to claim 7, wherein the inner frame component includes a plurality of arms coupled at the central portion and extending from the central portion to the outer frame component, separation of the central portion causes at least two of the arms to separate from each other to facilitate withdrawal of the hoisting frame.

9. The prosthesis according to claim 8, wherein each of the plurality of arms includes a free end coupled together at the central portion.

10. The prosthesis according to claim 9, wherein the free ends of the plurality of arms are coupled together with the tether.

11. The prosthesis according to claim 8, wherein the central portion is configured to be separated in a direction along the second axis of the self-expanding hoisting frame.

12. The prosthesis according to claim 8, wherein the central portion includes a separation region extending in the direction along the second axis.

13. The prosthesis according to claim 8, wherein the self-expanding hoisting frame is configured to be manipulated into a generally elongated configuration following separation of the central portion.

* * * * *

UNITED STATES PATENT AND TRADEMARK OFFICE
CERTIFICATE OF CORRECTION

| | |
|---|---|
| PATENT NO. | : 10,335,258 B2 |
| APPLICATION NO. | : 15/389943 |
| DATED | : July 2, 2019 |
| INVENTOR(S) | : Augustus Felix et al. |

Page 1 of 1

It is certified that error appears in the above-identified patent and that said Letters Patent is hereby corrected as shown below:

In the Specification

Column 10, Line 64, replace "releas ably" with --releasably--

Column 15, Line 47, replace "releas ably" with --releasably--

Signed and Sealed this
Twenty-third Day of June, 2020

Andrei Iancu
*Director of the United States Patent and Trademark Office*